United States Patent [19]

Leisinger et al.

[11] Patent Number: 5,787,600
[45] Date of Patent: Aug. 4, 1998

[54] DRYER MOUNTED IN A HOUSING

[75] Inventors: Roger Leisinger, Zürich; Eduard Fringeli, Bubikon; Bruno Nufer, Illnau, all of Switzerland

[73] Assignee: Mettler-Toledo AG, Greifensee, Switzerland

[21] Appl. No.: 729,189

[22] Filed: Oct. 11, 1996

[30] Foreign Application Priority Data

Dec. 12, 1995 [CH] Switzerland .......................... 03501/95

[51] Int. Cl.$^6$ .................................................. F26B 19/00
[52] U.S. Cl. ................................ 34/89; 34/197; 34/202; 117/144; 117/245
[58] Field of Search .......................... 34/60, 89, 177, 34/192, 194, 197, 202, 236, 237, 238; 177/144, 245

[56] References Cited

U.S. PATENT DOCUMENTS 1,493,222  5/1924  O'Neill ............................ 177/144
4,771,631  9/1988  Lehitkoski et al. ................. 73/73
4,932,486  6/1990  Komoto et al. .................... 177/50
5,437,108  8/1995  Alseth ........................... 34/238 X
5,485,684  1/1996  Phillipp et al. ................... 34/226
5,564,362  10/1996  Fiveash ......................... 119/51.5

FOREIGN PATENT DOCUMENTS 9315014  7/1994  Germany .

Primary Examiner—Henry A. Bennett
Assistant Examiner—Steve Gravini
Attorney, Agent, or Firm—Friedrich Kueffner

[57] ABSTRACT

A dryer mounted in a housing with a balance for determining the moisture content of material to be weighed which is in a dish placed in the balance and is subjected to a heat source. The dish is placed in a dish support device which can be placed in and removed from the dryer together with the dish. The dish can be inserted into the dish support device and removed from the dish support device manually and from the side. An upwardly bent inner edge of a support ring prevents impurities resting on the support ring from unintentionally dropping into the dish.

12 Claims, 3 Drawing Sheets

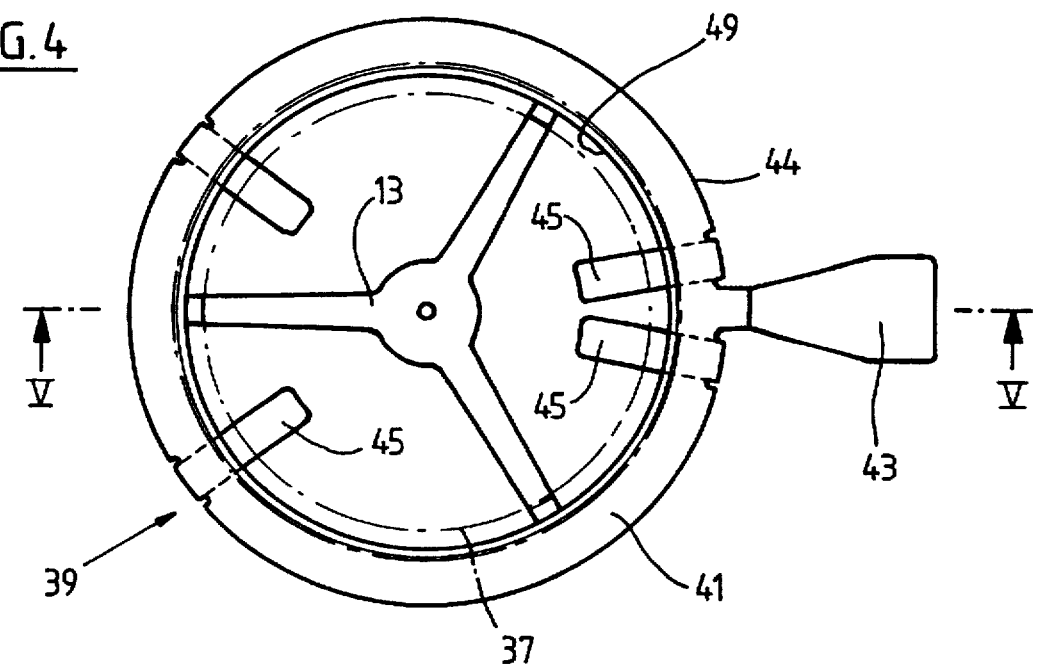
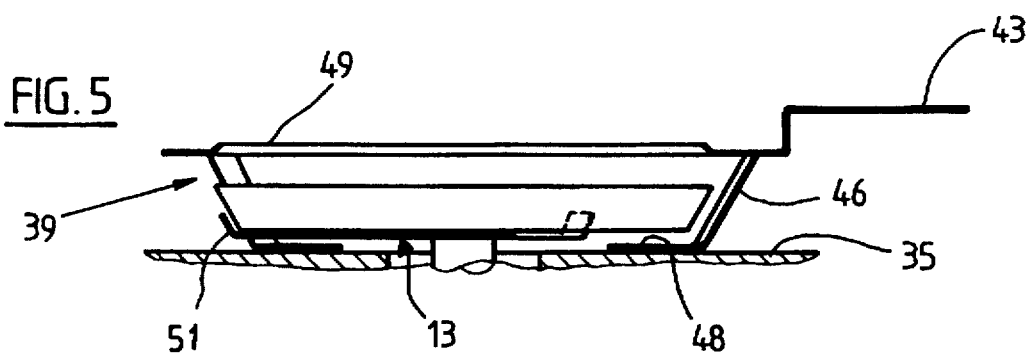

DRYER MOUNTED IN A HOUSING

BACKGROUND OF THE INVENTION

1. Field of the Invention

The present invention relates to a dryer mounted in a housing with a balance for determining the moisture content of material to be weighed which is in a dish placed in the balance and is subjected to a heat source.

2. Description of the Related Art

For determining the moisture content of a product, a sample of the product is dried in a suitable dish and the weight of the sample is measured before and after the drying procedure and possibly also during the drying procedure. The drying procedure is preferably carried out directly on a balance in order to avoid losses during the manipulation of the material to be dried and in order to be able to carry out the determination as quickly as possible.

A dryer of the above-described type is known from German Utility Model No. 93 15 014. In that device, the sample is placed on the weighing dish outside of the dryer. For this purpose, the balance is moved out of the dryer housing on a drawer-like pull-out member. The charging of the weighing dish with larger products to be weighed and placed individually on the weighing dish poses no problems. However, when pulverous or granular products are to be dried and weighed, there is the latent danger that portions of the material to be weighed drop during charging next to the weighing dish onto the balance and other parts of the pull-out member supporting the weighing dish. This is disadvantageous for two reasons. On the one hand, not the entire available material to be weighed is dried and weighed, and, on the other hand, the balance must be cleaned frequently.

SUMMARY OF THE INVENTION

Therefore, it is the primary object of the present invention to provide a dryer which makes it possible to charge the material to be weighed without losses and in a simple manner.

In accordance with the present invention, a dryer is provided in which the dish is placed in a dish support device which can be placed in and removed from the dryer together with the dish.

The dish support device according to the present invention makes it possible to charge the dish with material to be weighed outside of the balance and the dish can then be placed in the balance within the dryer, i.e., on the material support means of the balance in the form of a dish carrier, without having material to be weighed fall out and loosing the material for the weighing procedure; in addition, the balance cannot be contaminated. On the other hand, the hot dish can be removed from the dryer after the drying and weighing procedure of the material to be weighed, without burning the fingers and also without spilling material to be weighed. The dish support device is not being weighed because the dish is raised from the dish support device when the dish is placed on the balance.

The dish can be inserted into the dish support device and removed from the dish support device manually and from the side An upwardly bent inner edge of a support ring prevents impurities resting on the support ring from unintentionally dropping into the dish.

In accordance with another further development of the invention, the dish can be placed in the dish support device from below and can be secured in the dish support device.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

FIG. 4 is a top view of another embodiment of a dish support device within a dryer, shown without dish;

FIG. 5 is a longitudinal sectional view of the dish support device with dish inserted, taken along sectional line V—V in FIG. 4;

FIG. 6 is a plan view of a dish carrier;

DESCRIPTION OF THE PREFERRED EMBODIMENTS

Figure 1:
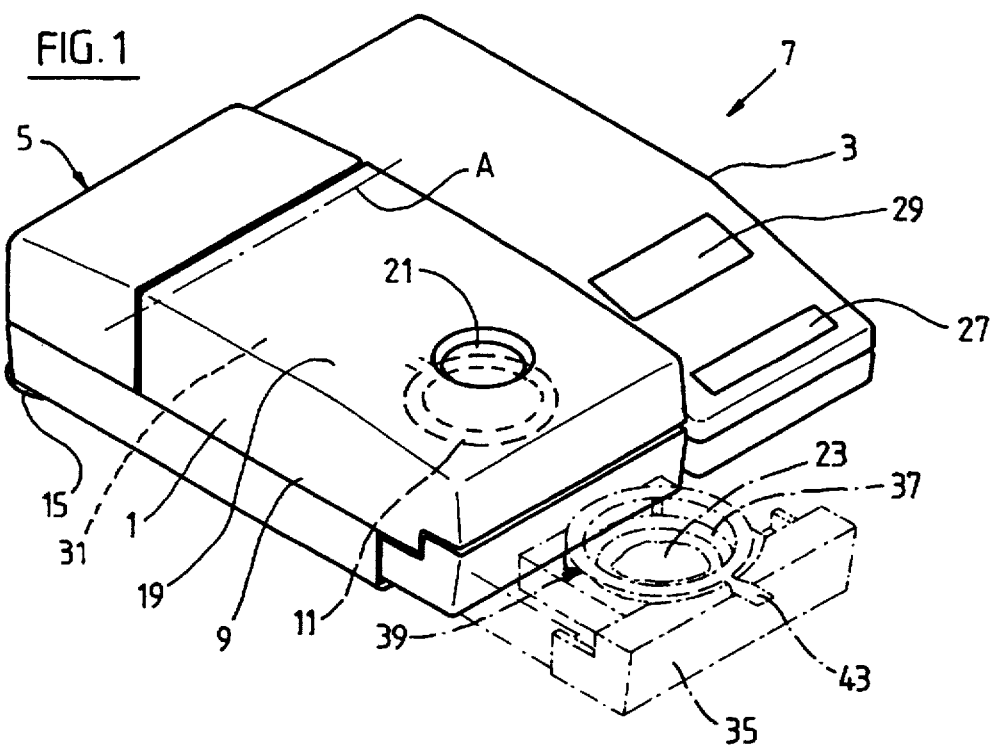
FIG. 1 is a schematic perspective illustration of a dryer.

As shown in FIG. 1 of the drawing, a drying apparatus or dryer 7 of the known type has a housing 5 composed of two parts 1 and 3. Mounted in part 1 are a balance and weighing unit 9 and a heat source 11. Part 3 of the housing is arranged laterally adjacent to part 1. Part 3 contains the control and display elements. Electronic components for the balance 9 may also be mounted in part 3.

The front portion of the upper part of part 1 is constructed as a cover 19 and can be swung upwardly about a horizontal axis A. An inspection glass 21 may be placed in the cover 19 to make it possible to view a dish 37 placed on a dish carrier 13 and the material 23 placed on the dish 37. The inspection glass 21 is located concentrically relative to the heat source 11. In the illustrated embodiment, the heat source 11 is an essentially ring-shaped halogen lamp which heats and illuminates the drying space located between the dish carrier 13 and the cover 19.

A keyboard 27 and a display area 29 are arranged on the upper side of the part 3 for displaying and controlling the functions of the balance 9 and the dryer 7. The configuration of the control and display elements is not explained in detail since they are not subject of the invention.

The dryer 7 is supported on legs 15 for exactly horizontally levelling the dryer 7.

The balance 9 including the measuring cell 31 thereof and the dish carrier 13 are placed in a drawer-like pull-out member 35 and are mounted on a linear guide so as to be moveable out of the housing 5. The dish 37 is placed within a dish support device 39 which shall be described in more detail below.

The dish support device 39 includes a circular ring-shaped support member 41 which is connected to a radially outwardly projecting gripping lug 43. Attached to the outer rim 44 of the support member 41 are three lugs 45 which are directed downwardly and toward the center. The front ends 47 of the lugs 45 are located at a distance from the center of symmetry of the support ring 41 and form a central passage opening.

The upper portions 46 of the support lugs 45 extend from the outer rim 44 of the support ring 41 either vertically or downwardly at an acute angle relative to the bottom side of the support ring 41. The lower portions 48 of the lugs 45 extend in a common plane and form the support surfaces of the dish support device 39 outside as well as inside the dryer 7.

Figure 2:
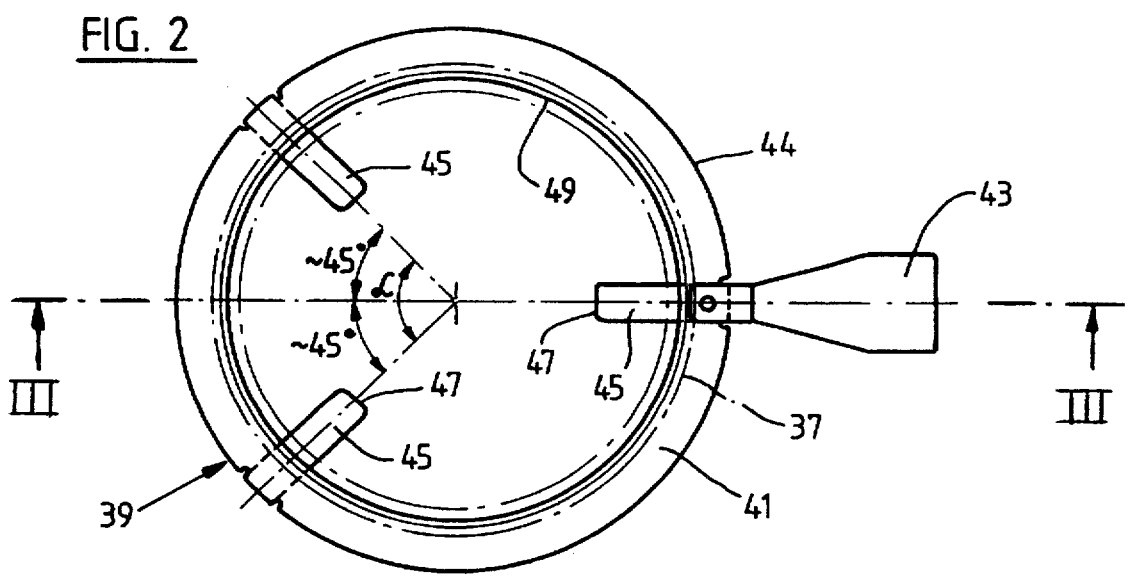
FIG. 2 is a top view of a dish support device.
Figure 3:
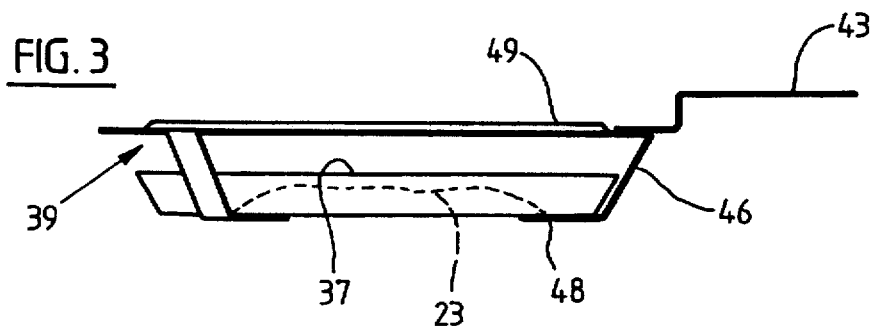
FIG. 3 is a longitudinal sectional view of the dish support device with a dish being placed in the dish support device, taken along sectional line III—III of FIG. 2.

One of the support lugs 45 is arranged underneath the gripping lug 43. The two other support lugs 45 are arranged symmetrically opposite the first support lug 45, wherein the oppositely located two support lugs 45 include an angle α therebetween of approximately 90°. The support ring 41 and the support lugs 45 may be punched from a single piece of sheet metal and subsequently shaped, for example, by bending, deep-drawing, etc., into the position shown in FIGS. 2 and 3. The gripping lug 43 can also be connected to the support ring 41 by welding, riveting or gluing.

In accordance with a preferred further development, the inner edge 49 of the support ring 41 is bent upwardly.

In the second embodiment of the dish support device 39 according to the invention shown in FIG. 4, two support lugs 45 are provided on the side of the gripping lug 43. This embodiment makes it possible to construct the entire dish support device 39 from a single piece of sheet metal and to obtain the desired shape solely by punching and bending operations. It is not necessary to use rivets which could become loose or could collect impurities.

In the following, the manner of manipulating the dish support 39 according to the present invention shall be explained in more detail. Starting from a dish 37 which is located outside of the dryer 7, the following steps are carried out. The dish 37 is pushed manually from the side underneath the support ring 41 onto the support lugs 45. When material 23 has already been placed on the dish 37, the dish 37, held at the gripping lug 43, can be placed together with the dish support device 39 onto the dish carrier 13 in the dryer 7. The dish 37 is placed on the dish carrier 13, i.e., placed on the balance 9, when the dish support device 39 is put down in the dryer 7.

The arms 51 of the dish carrier 13 come to rest between the support lugs 45 of the dish support device 39 when the dish support device 39 is lowered. The lower portions 48 of the support lugs 45 rest in the dryer 7 on the drawer 35 in a housing surrounding the measuring cell of the balance 9. For dishes 37 having very small diameters, it would also be sufficient to use a dish carrier 13 having a circular support surface 53 which is placed between the ends 47 of the support lugs 45, as shown in FIG. 4.

Figure 7:
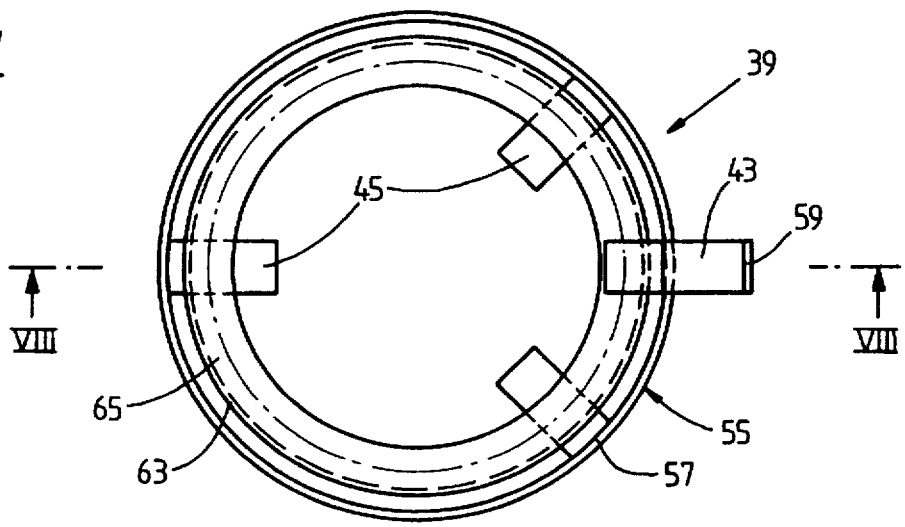
FIG. 7 is a top view of a two-part dish support device.
Figure 8:
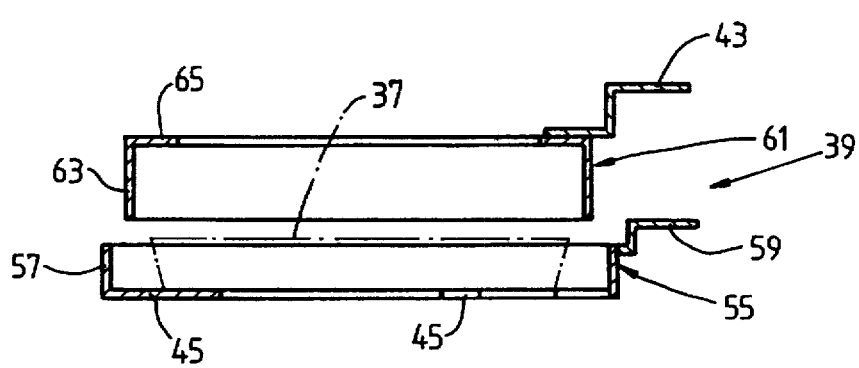
FIG. 8 is a sectional view of the dish support device of FIG. 7 taken along sectional line VIII—VIII, wherein the upper part and the lower part are shown separately.

In the embodiment of the present invention illustrated in FIGS. 7 and 8, the dish support device 39 is composed of two parts and includes a lower part 55 which includes integrally connected support lugs 45 corresponding to the support lugs 45 of the first two embodiments. The lower part 55 includes a cylindrical collar or portion 57 to which the support lugs and a lower gripping lug 59 are fastened. The lower gripping lug 59 and the upper gripping lug 43 are of similar shape, and, when the upper part 61 which is also of cylindrical shape is placed onto the lower part 55, the lower gripping lug 59 rests from below against the upper gripping lug 43. In addition to the cylindrical portion 63, the upper part 61 includes a circular ring-shaped support ring 65 connected to the top of the portion 63, wherein the gripping lug 43 is fastened to the support ring 65. The inner diameter of the cylindrical portion 57 of the lower part 55 is greater than the outer diameter of the cylindrical portion 63 of the upper part 61. As a result, the two parts, i.e., the lower part 55 and the upper part 61 can be placed into one another. This is done after the dish 37 has been placed in the lower part 55.

Figure 9:
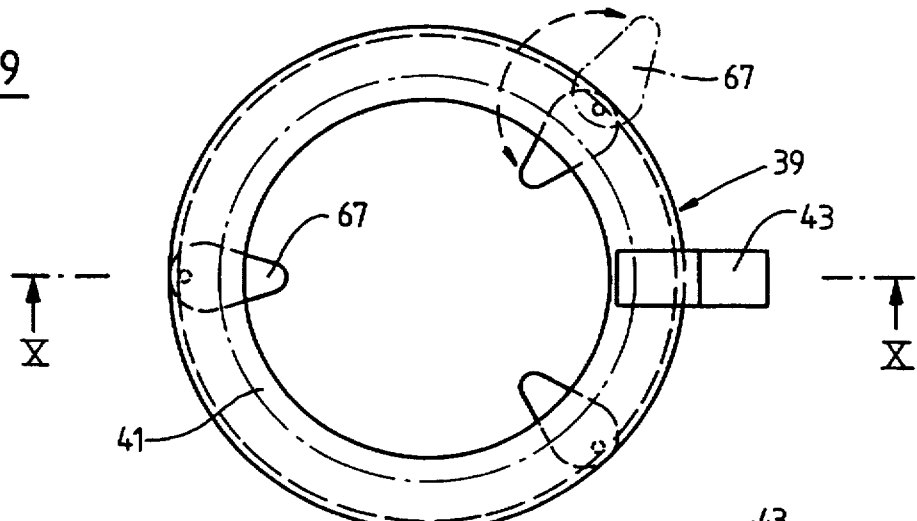
FIG. 9 is a top view of another embodiment of a dish support vice with swingable support lugs.
Figure 10:
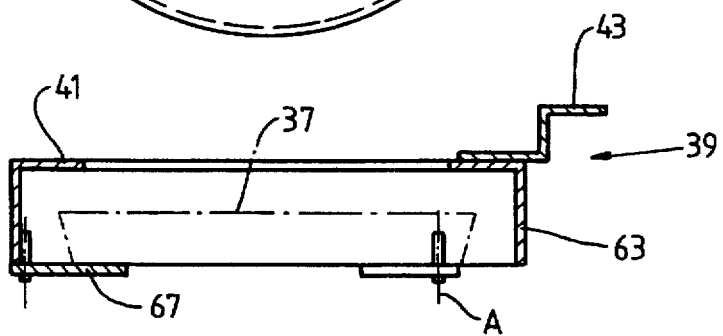
FIG. 10 is a sectional view of the dish support device of FIG. 9, taken along sectional line X—X.

In the embodiment of the present invention shown in FIGS. 9 and 10, the dish support device 39 is of similar construction as in the embodiments of FIGS. 2 to 5. The difference of this embodiment is that, in the same manner as in FIGS. 7 and 8, a cylindrical collar or portion 63 laterally closes off the dish support device 39. The portion 63 is at the top thereof connected to the circular ring-shaped portion 41. In turn, the gripping lug 43 is connected to the portion 41. For placing the dish 37 into the dish support device 39, three lugs 67 which are swingable about vertical axes are hinged to the cylindrical portion 63. For receiving the dish 37, the lugs 67 are swung toward the outside, as shown at the top of FIG. 9. In the illustrated example, the lugs 67 can be swung individually. However, they may also be connected to each other through appropriate means for synchronously swinging the lugs 67 in and out. The configuration of such a swinging device is not shown in detail; it may correspond to that of a shutter of camera.

If the material 23 to be weighed has not already been placed on the dish 37 outside of the dryer 7, this can also been done directly when the drawer 35 is pulled out. Any material 23 spilled next to the dish 37 as a result of a careless manipulation comes to rest on the support ring 41 and cannot contaminate the interior of the dryer 7. It is also possible to determine precisely what portion of the material 23 has been spilled and did not drop into the dish 37. Spilled material 23 does not falsify the measurement because the dish support device 39 does not rest on the balance 9 and is also not being weighed as a result. Any material 23 which has been spilled onto the support ring 41 can also not drop inadvertently into the dish 37 at a later time; this is prevented by the upwardly bent edge 49.

After the drying and weighing procedures have been carried out, the hot dish 37 can be removed from the dryer 7 immediately together with the dish support device 39. Consequently, for handling the dish 37, it is not necessary that the dish first cools down.

While specific embodiments of the invention have been shown and described in detail to illustrate the inventive principles, it will be understood that the invention may be embodied otherwise without departing from such principles.

We claim:

1. A dryer mounted with a balance in a housing for determining the moisture content of material to be weighed which is subjected to a heat source, comprising a stationary dish carrier connected to the balance and a dish for receiving the material to be weighed and to be placed on the dish carrier, further comprising a dish support device movable together with the dish for placing the dish on the dish carrier and for removing the dish from the dish carrier.

2. The dryer according to claim 1, wherein the dish support device comprises a support ring and a plurality of support lugs for receiving the dish, the support lugs being attached to the support ring and being directed inwardly toward a center of the support ring.

3. The dryer according to claim 2, wherein each support lug comprises a first portion extending downwardly from the support ring and a second inwardly extending portion connected to the first portion.

4. The dryer according to claim 2, wherein each support lug is attached so as to be swingable about a vertical axis relative to the support ring.

5. The dryer according to claim 2, wherein the dish support device comprises a cylindrical portion connected to the support ring, and wherein each support lug is attached so as to be swingable about a vertical axis relative to the cylindrical portion.

6. The dryer according to claim 1, wherein the dish support device comprises an upper part and a lower part, the upper part and the lower part each having a cylindrical portion, wherein the cylindrical portion of the upper part is insertable into the cylindrical portion of the lower part.

7. The dryer according to claim 6, comprising a plurality of support lugs for receiving the dish, the support lugs being fastened to the cylindrical portion of the lower part.

8. The dryer according to claim 1, comprising a gripping lug attached to the dish support device.

9. The dryer according to claim 2, wherein the dish support device is a member punched from a sheet metal part with downwardly and inwardly bent support lugs.

10. The dryer according to claim 2, wherein the support ring comprises an upwardly bent inner edge.

11. The dryer according to claim 2, wherein the support lugs are arranged radially extending from the circumference.

12. The dryer according to claim 2, wherein the dish carrier has radially arranged arms located between the support lugs of the dish support device.

* * * * *